(12) United States Patent
Kear

(10) Patent No.: US 7,189,223 B2
(45) Date of Patent: Mar. 13, 2007

(54) DUAL SHORT THROW ADVANCER/RETRACTOR

(75) Inventor: Jason W. Kear, Bloomington, IN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 106 days.

(21) Appl. No.: 10/757,763

(22) Filed: Jan. 14, 2004

(65) Prior Publication Data

US 2004/0147923 A1  Jul. 29, 2004

Related U.S. Application Data

(63) Continuation of application No. 10/175,673, filed on Jun. 19, 2002, now Pat. No. 6,736,812.

(51) Int. Cl.
*A61B 17/00* (2006.01)
*A61B 18/18* (2006.01)

(52) U.S. Cl. ............................. 606/1; 606/46
(58) Field of Classification Search ............ 606/45–47, 606/51, 52, 205, 206, 1; 600/562–567
See application file for complete search history.

(56) References Cited

U.S. PATENT DOCUMENTS

| 4,905,691 | A |   | 3/1990 | Rydell |
| 5,035,696 | A |   | 7/1991 | Rydell |
| 5,147,373 | A | * | 9/1992 | Ferzli .................... 606/144 |
| 5,290,284 | A | * | 3/1994 | Adair ..................... 606/37 |
| 5,376,094 | A |   | 12/1994 | Kline |
| 5,997,547 | A |   | 12/1999 | Nakao et al. |
| 6,007,546 | A |   | 12/1999 | Snow et al. |
| 6,050,995 | A |   | 4/2000 | Durgin |
| 6,352,539 | B1 |  | 3/2002 | Avellanet |

FOREIGN PATENT DOCUMENTS

EP  0 705 569 A1  4/1996
WO  WO 00/06033  2/2000

OTHER PUBLICATIONS

"Sensation™ Single-Use Medium Stiff Wire Short Throw Snares" and "Sensation™ Single-Use Short Throw Snares," *2002 Price List and Ordering Information: Products for Endoscopy*, Boston Scientific MICROVASIVE, 2002, 3 pages.

* cited by examiner

*Primary Examiner*—Michael Peffley
(74) *Attorney, Agent, or Firm*—Christensen O'Connor Johnson Kindness PLLC

(57) ABSTRACT

A dual throw advancer/retractor has a pair of finger rings that can independently advance or retract a medical device into a catheter. The advancer/retractor has a body and a channel wherein each finger ring moves independently in the channel. One end of the medical device is preferably secured to the body and forms a loop within the finger ring such that movement of the finger ring creates an amplified movement in the medical device.

5 Claims, 4 Drawing Sheets

DUAL SHORT THROW ADVANCER/RETRACTOR

CROSS-REFERENCE TO RELATED APPLICATION

This application is a continuation of U.S. application Ser. No. 10/175,673, filed Jun. 19, 2002 now U.S. Pat. No. 6,736,812.

FIELD OF THE INVENTION

The present invention relates to medical devices in general and in particular to advancers and retractors to be used with endoscopes.

BACKGROUND OF THE INVENTION

In many surgical situations, physicians prefer to use tools that allow them to perform multiple tasks with minimal movement. Such tools can be not only less expensive than requiring the purchase of multiple tools that perform a single task but can be more efficient during use.

One situation where efficiency is required is during an endoscopic examination and tissue removal procedure. To remove tissue such as a polyp or other area of interest, a physician typically views the tissue in question with an endoscope. A catheter having a long needle is passed down a lumen in the endoscope and a liquid, such as saline, is injected under the tissue in question in order to raise it from the surrounding tissue. The needle and catheter are then withdrawn from the endoscope and a cauterizing catheter having a wire snare is inserted through the endoscope to remove and cauterize the tissue.

While this method can work well, two catheters are always required and it takes time for the physician to withdraw the first and insert the second. Therefore, there is a need for a device that allows a physician to manipulate two medical devices in a single catheter.

SUMMARY OF THE INVENTION

A dual advancer/retractor in accordance with the present invention includes a handle body and a pair of independently moveable finger rings. Each finger ring is adapted to advance or retract a medical device. In one embodiment of the invention, each medical device has an end secured to the handle body and a length which forms a loop within the finger rings such that movement of the finger rings causes an amplified movement of the medical device into and out of a catheter.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
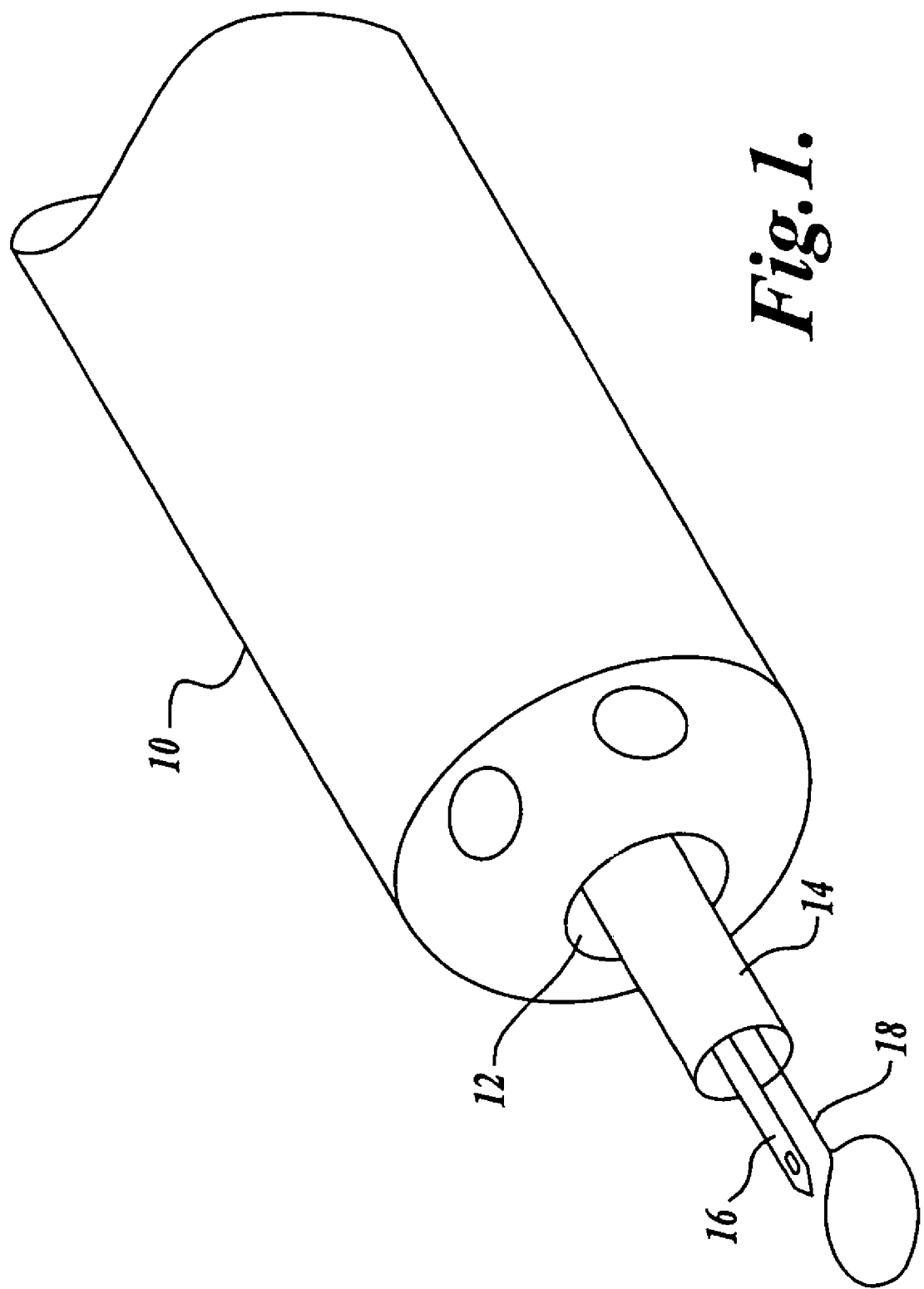
FIG. 1 illustrates a portion of an endoscope with a catheter having two medical devices contained therein to allow a physician to perform multiple tasks with the same catheter.

FIG. 1 illustrates a portion of an endoscope 10 having a lumen 12 that extends along its length through which medical devices may be routed. In the example shown, the medical device is a catheter 14 having a needle 16 and an electro-cauterizing snare 18 that can be individually advanced out of or retracted into the end of the catheter 14.

During a surgical procedure to remove certain types of tissue, the physician advances the needle 16 out of the catheter and into a tissue area in order to inject a liquid underneath the tissue. The needle 16 is then withdrawn into the catheter 14 and the snare 18 is then advanced out of the catheter and looped over the raised tissue. The snare is then tightened around the base of the tissue and an electrical current is applied to the snare to remove the tissue and cauterize the removal site. As will be explained in further detail below, the present invention allows a physician to independently advance or retract the needle 16 and snare 18 from the catheter with a single handheld advancer/retractor.

Figure 2:
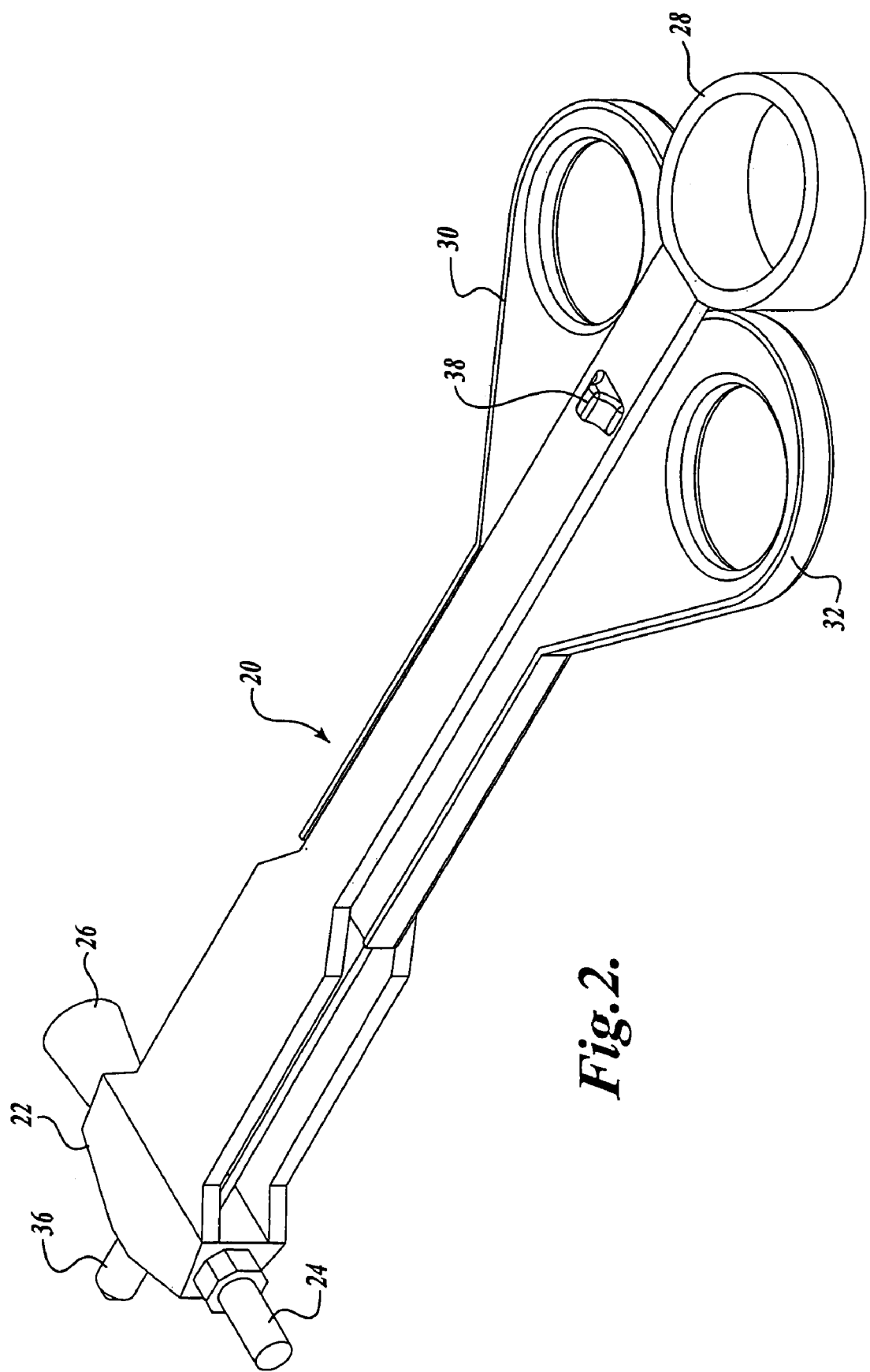
FIG. 2 is an isometric view of a dual, short throw advancer/retractor in accordance with an embodiment of the present invention.

FIG. 2 is an isometric view of a dual throw, advancer/retractor 20 in accordance with one embodiment of the present invention. The advancer/retractor 20 includes an elongated body 22 having connectors 24 and 26 positioned on opposite sides of its distal end and a thumb ring 28 at its proximal end. A pair of finger rings 30, 32 slide in a channel along the length of the advancer/retractor 20 between the proximal and distal end in order to independently advance or retract a medical device from a catheter. Each of the finger rings 30, 32, can be advanced distally in the channel until it engages the distal end of the body 22. The thumb ring 28, limits the movement of the finger rings 30, 32, in the channel when moved in the proximal direction.

A connector 36 is positioned at the distal tip of the body 22 to allow the advancer/retractor 20 to be coupled to a catheter (not shown) by a friction fit or other securing mechanism such as a lever lock. A lock 38 is positioned near the proximal end of the body 22 to allow a user to lock either of the finger rings 30, 32, such that it cannot be advanced or retracted in the channel. When one finger ring is secured with the lock, the other finger ring is preferably free to move. However, the lock may be designed to secure the position of both finger rings at once.

Figure 3:
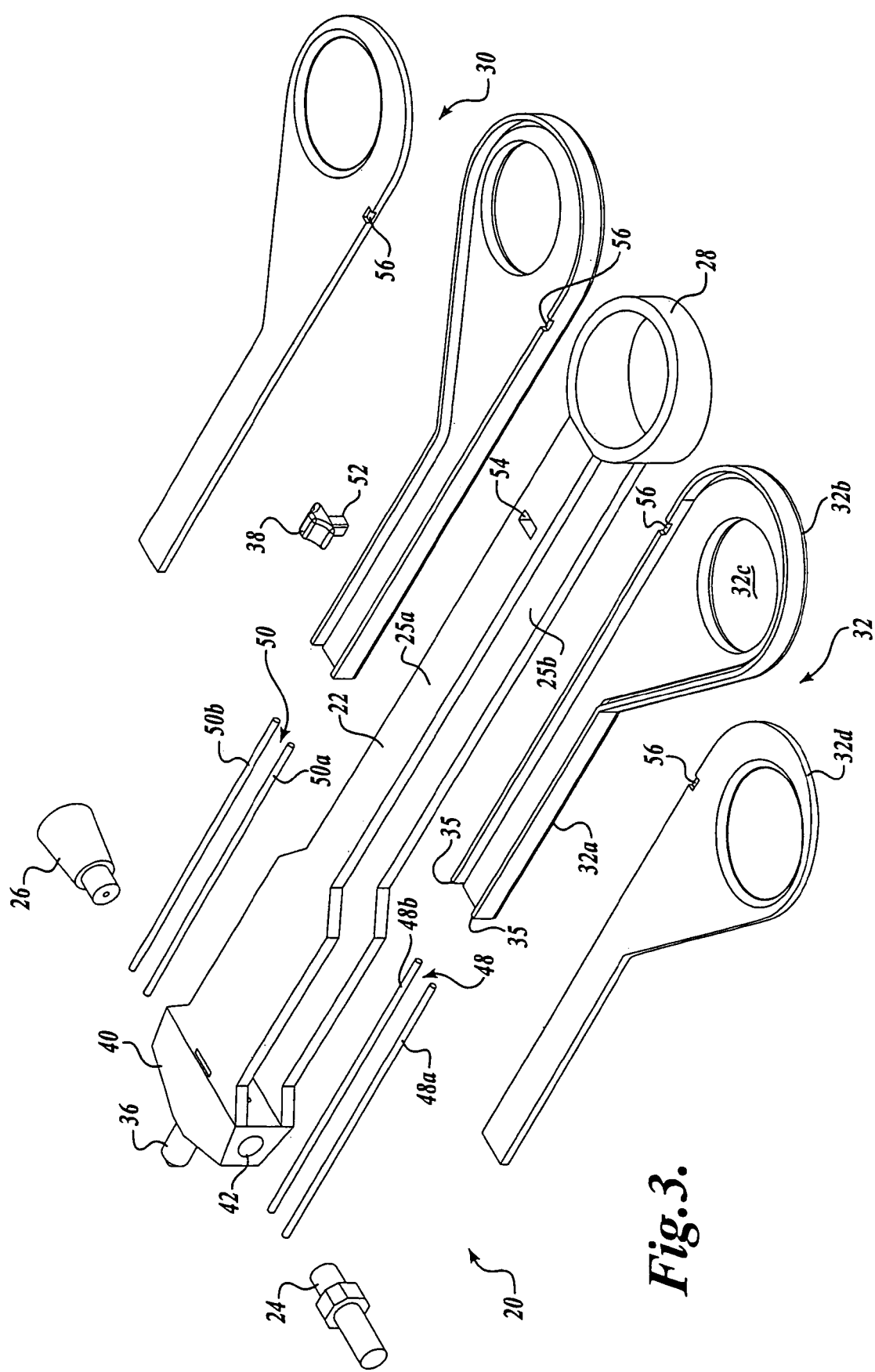
FIG. 3 is an exploded view of the dual, short throw advancer/retractor shown in FIG. 2.

FIG. 3 is an exploded view of the dual throw advancer/retractor 20 shown in FIG. 2. The elongated body 22 has a distal end 40 that comprises a generally solid block having a hole 42 on its side into which the port 24 is fitted. The distal end 40 includes another hole (not shown) on the opposite side into which the port 26 is fitted. Each port 24, 26 allows a device such as an electrosurgical cutter or liquid source etc. to be connected to a medical device advanced or retracted by the corresponding finger ring. Connecting the distal end 40 and the thumb ring 28 is a top plate 25a and a bottom plate 25b. The space between the plates forms the channel in which the finger rings 30, 32 can slide.

To keep the finger rings in the channel, the advancer/retractor 20 includes at least one rod 48 that is associated with the finger ring 32 and at least one rod 50 that is associated with the finger ring 30. Each rod has an end that is secured to the distal end 40 of the body 22 and a free end that extends into the channel. The rods 48, 50 act as guide rails over which the finger rings 30, 32 slide, in order to keep the finger rings in the channel.

Each of the finger rings 30, 32, is formed of a top and bottom half that are ultrasonically welded together or secured by an adhesive or the like. The finger ring 32 includes a generally straight section 32a in which the rod 48 is received and a flared proximal section 32b that extends radially outward. The sides of the finger rings where they meet along the center of the channel are generally straight. A groove 35 extends around the inner edge of the finger ring 32. The groove 35 forms a track in which the rod 48 travels and forms a path in which a medical device is held, as will be described below. In one embodiment of the invention, each finger ring, e.g. finger ring 32, has two rods 48a, 48b that slide within the groove 35 to hold the finger ring in the channel. Although the embodiment of the invention shown uses rods to hold the finger rings in the channel, it will be appreciated that other mechanisms such as a cooperating shape on the top or bottom plate 25a, 25b and the inner surface of the finger ring channel could also be used to keep the finger rings within the channel.

The flared section 32b of the finger ring also includes a hole 32c into which a user can insert their finger. A top half 32d of the finger ring has a similar shape to the bottom half such that the two halves can be fitted together to complete the finger ring 32.

Each finger ring 30, 32 also includes a notch 56 that is used to secure the position of the finger ring in the channel. The lock 38 has a post 52 that is fitted within a slot 54 on the top plate 25a of the body 22. The lock 38 is moveable within the slot 54 such that the post 52 selectively engages the slot 56 on the finger rings 30, 32. If the post 52 is engaged in the notch 56, the position of the finger ring is fixed in the channel. By moving the lock 38 to one side or the other in the slot 54, either finger ring can be secured.

Figure 4:
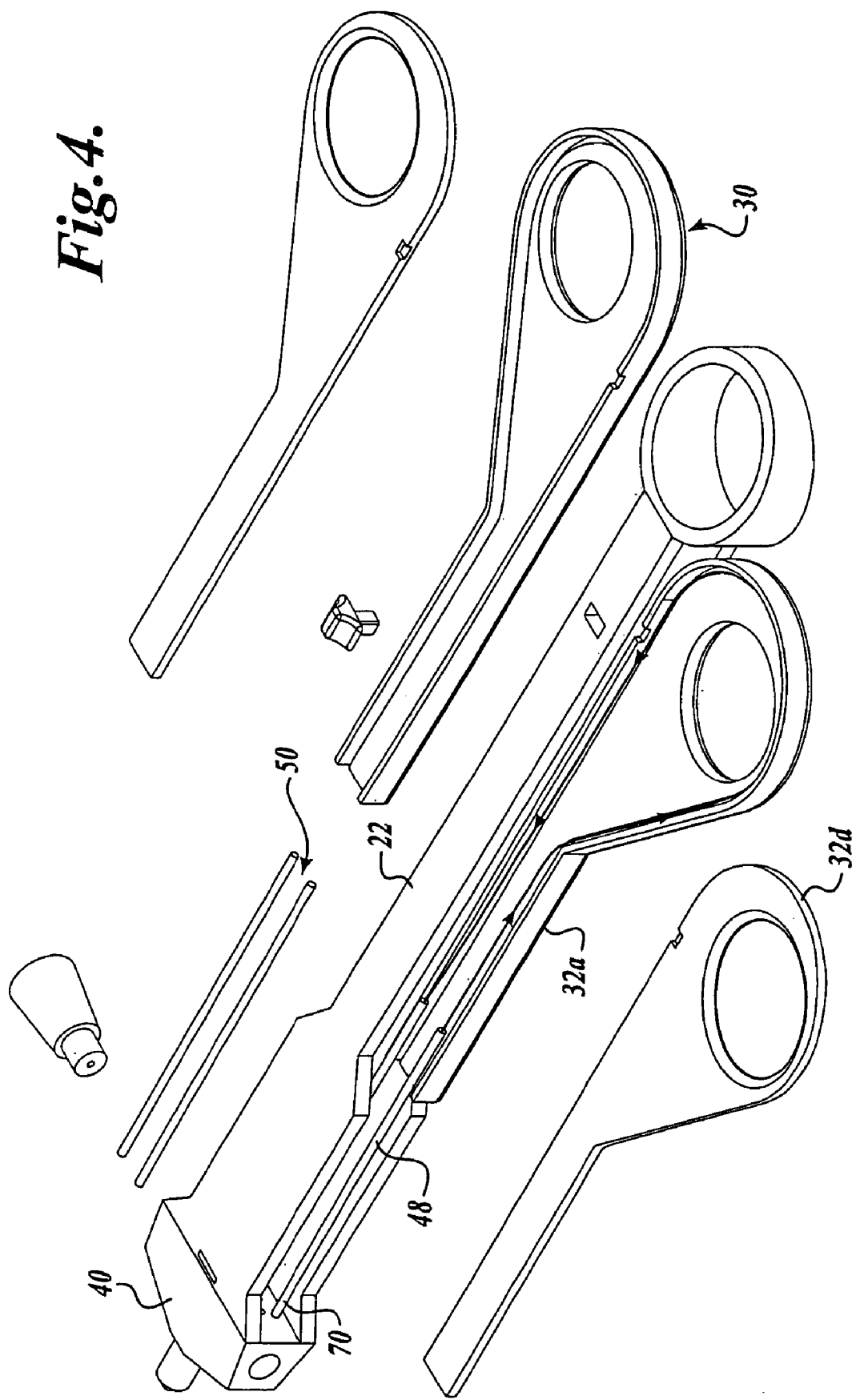
FIG. 4 illustrates one method for constructing the dual, short throw advancer/retractor shown in FIG. 2.

FIG. 4 illustrates in further detail how the advancer/retractor 20 is assembled. The rods 48a, 48b, 50a, 50b are secured to the distal end 40 of the advancer/retractor body such that they extend proximally in the channel. In one embodiment of the present invention, each of the rods is hollow and a medical device such as a wire or hypo tube is passed through the hole in the rods. The hollow rods both maintain the finger rings in the channel and provide support for the medical devices so they don't kink or bend as the finger ring is advanced. However, other mechanisms such as a molded slot might be used to provide support for the medical devices if desired. The medical device lies within the groove 35 such that it extends proximally and loops around the outside of the hole in the finger ring before returning through the hollow rod 48b and exiting the body 22 at the connector 36. The finger ring thereby acts as a pulley. Each medical device preferably has one end secured at the distal end 40 of the advancer/retractor. In one embodiment, each medical device has an end that is secured within the rods positioned on the outside edge of the channel. As indicated above, the hole 32c in the finger ring forms a pulley around which the medical device is looped. By fixing one end of the medical device to the body of the advancer/retractor, movement of the finger ring in the channel causes an amplified movement of the medical device into and out of the catheter. As will be appreciated, it is not necessary that the medical device be passed around the outside of the hole in the finger ring. A tighter return bend could be positioned elsewhere in the finger ring if the medical device is sufficiently flexible.

To assemble the advancer/retractor, the medical device is threaded through the holes in the rods 48a, 48b and has one end secured in the outside rod using an adhesive, soldering, welding, crimping, etc. The straight portion 32a of the finger ring is positioned such that the rods 48a, 48b align with the groove 35 on either side of the straight portion 32a of the finger ring. The top half 32d of the finger ring is then secured to the bottom half with an adhesive or with ultrasonic welding or the like to complete the finger ring. With the rods extending into the channel of the finger ring, the finger ring is held in place in the body 22 of the advancer retractor. The finger ring 30 is generally a mirror image of the finger ring 32 and is assembled in the same way.

As indicated above, each of the ports 24, 26 allow devices such as an electrosurgical generator to be connected to the corresponding medical device moved by the finger ring. In the case of an electrical snare, the port must allow the rods in which the snare is located to be contacted electrically. In the case of a hypo tube, the port should allow a fluid to be pushed into or out of the rod in which the hypo tube is located. The hypo tube should have one or more holes at its proximal end to allow the fluid to enter the lumen of the hypo tube.

While the preferred embodiment of the invention has been illustrated and described, it will be appreciated that various changes can be made therein without departing from the spirit and scope of the invention. For example, the advancer/retractor is not limited to use with hypo tubes or wire snares. Any medical device that is sufficiently flexible to be moved by the finger ring could be used. It is therefore intended that the scope of the invention be determined from the following claims and equivalents thereof.

The embodiments of the invention in which an exclusive property or privilege is claimed are defined as follows:

1. An advancer/retractor, comprising:
    a handle body having, at least, a first medical device and a second medical device secured thereto;
    a first grip connected to the handle body and to the first medical device, wherein movement of the first grip causes an amplified movement of the first medical device; and
    a second grip connected to the handle body and to the second medical device, wherein movement of the second grip causes an amplified movement of the second medical device, wherein the first grip includes a first pulley around which the first medical device is looped and the second grip includes a second pulley around which the second medical device is looped.

2. The advancer/retractor of claim 1, wherein the first and the second grips are independently advanced or retracted.

3. An advancer/retractor, comprising:
    a handle body having, at least, a first medical device and a second medical device secured thereto;
    a first grip connected to the handle body and to the first medical device, wherein movement of the first grip causes an amplified movement of the first medical device; and
    a second grip connected to the handle body and to the second medical device, wherein movement of the second grip causes an amplified movement of the second medical device, wherein the first grip includes a finger ring which forms a first pulley and the second grip includes a finger ring which forms a second pulley.

4. An advancer/retractor, comprising:
    a handle body having, at least, a first medical device and a second medical device secured thereto;
    a first grip connected to the handle body and to the first medical device, wherein movement of the first grip causes an amplified movement of the first medical device; and a second grip connected to the handle body and to the second medical device, wherein movement of the second grip causes an amplified movement of the second medical device, further comprising a catheter coupled to the handle body, wherein the first medical device passes through the catheter and is advanced and retracted into and out of the catheter with movement of the first grip and the second medical device passes through the catheter and is advanced and retracted into and out of the catheter with movement of the second grip.

5. An advancer/retractor, comprising:

a handle body having, at least, a first medical device and a second medical device secured thereto;

a first grip connected to the handle body and to the first medical device, wherein movement of the first grip causes an amplified movement of the first medical device; and a second grip connected to the handle body and to the second medical device, wherein movement of the second grip causes an amplified movement of the second medical device, wherein the first medical device includes a flexible portion which forms a loop at the first grip and the second medical device includes a flexible portion which forms a loop at the second grip.

* * * * *

UNITED STATES PATENT AND TRADEMARK OFFICE
CERTIFICATE OF CORRECTION

PATENT NO. : 7,189,223 B2
APPLICATION NO. : 10/757763
DATED : March 13, 2007
INVENTOR(S) : J.W. Kear It is certified that error appears in the above-identified patent and that said Letters Patent is hereby corrected as shown below:

| COLUMN | LINE | ERROR |
|---|---|---|
| On Title Page Item (*) and Item 45 Pg. 1, col. 1 | Notice | indent and insert after the sentence "Subject to any disclaimer...106 days." --This patent is subject to a terminial disclaimer.-- |

Signed and Sealed this

Twenty-eighth Day of August, 2007

JON W. DUDAS
*Director of the United States Patent and Trademark Office*